United States Patent [19]

Yun et al.

[11] Patent Number: 4,503,146

[45] Date of Patent: Mar. 5, 1985

[54] METHOD FOR ELIMINATING TURBIDITY IN A BIOLOGICAL FLUID AND REAGENT THEREFOR

[75] Inventors: Shyun-long Yun, Tarrytown, N.Y.; Luis P. León, Fairfield, Conn.; Syed I. Ahmad, Orangeburg, N.Y.

[73] Assignee: Technicon Instruments Corporation, Tarrytown, N.Y.

[21] Appl. No.: 482,201

[22] Filed: Apr. 5, 1983

Related U.S. Application Data

[63] Continuation of Ser. No. 192,651, Oct. 1, 1980, abandoned.

[51] Int. Cl.³ .................... C12Q 1/44; C12Q 1/34; C12Q 1/60; C12Q 1/00
[52] U.S. Cl. .................... 435/19; 435/11; 435/18; 435/4; 436/175; 436/71; 436/13; 436/15; 436/17
[58] Field of Search ............ 435/4, 11, 17, 18, 19, 435/25, 28, 188; 436/15, 13, 17, 71, 175; 23/909

[56] References Cited

U.S. PATENT DOCUMENTS

| | | | |
|---|---|---|---|
| 3,594,325 | 7/1971 | Feierstein et al. | 435/188 |
| 3,775,331 | 11/1973 | Borrello | 435/188 |
| 4,066,508 | 1/1978 | Rauscher et al. | 435/26 |
| 4,226,713 | 10/1980 | Goldberg et al. | 23/230 B |
| 4,282,001 | 8/1981 | Klose et al. | 23/230 B |
| 4,292,038 | 9/1981 | Kondo et al. | 252/408 |
| 4,414,326 | 11/1983 | Goldberg | 435/28 |

FOREIGN PATENT DOCUMENTS

| | | | |
|---|---|---|---|
| 0847837 | 7/1970 | Canada | 252/408 |
| WO80/02697 | 12/1980 | PCT Int'l Appl. | 435/19 |

OTHER PUBLICATIONS

Esders et al, "Hydrolysis of Protein Bound Cholesterol Esters." Chemical Abstracts 89:159794w.

*Primary Examiner*—Thomas G. Wiseman
*Assistant Examiner*—J. P. Tarcza
*Attorney, Agent, or Firm*—Morgan, Finnegan, Pine, Foley & Lee

[57] ABSTRACT

A method for eliminating turbidity in a biological fluid by combining said fluid with a surfactant and an enzyme is disclosed as well as a diagnostic reagent formulation for that purpose.

31 Claims, No Drawings

METHOD FOR ELIMINATING TURBIDITY IN A BIOLOGICAL FLUID AND REAGENT THEREFOR

CROSS-REFERENCE TO RELATED APPLICATIONS

This application is a continuation of application Ser. No. 192,651, filed Oct. 1, 1980 now abandoned.

BACKGROUND OF THE INVENTION

This invention relates generally to a method for effectively clearing turbidity in a biological sample such as human serum and to a reagent used for that purpose. More particularly, it relates to a reagent comprised of a surfactant and an enzyme and to its application as a turbidity-removing agent.

Turbidity in a biological sample can cause severe problems. It results in poor or incorrect readings and therefore highly questionable determinations.

Turbidity in serum and plasma samples is usually a serious problem in clinical photometric analysis. It gives false data and often yields misleading photometric determinations of serum ingredients. The turbidity is believed caused primarily by the elevation of triglycerides in serum of patients having hyperlipoproteinemia with or without elevated total cholesterol. Abnormal elevation of cholesterol in serum has been shown to correlate with a high risk artherosclerosis. Determination of cholesterol and triglycerides is important since accurate data will help the doctor to diagnose patients with hyperlipoproteinemia and to predict certain heart disease. Other tests such as aspartate aminotransferase (GOT), alanine aminotransferase (GPT) and lactate dehydrogenase (LDH), etc. have also suffered from the same difficulties as cholesterol or triglyceride determination, as mentioned above, when turbid samples are examined.

Clinical tests of turbid serum has been handled by treating samples with high concentration of surfactants such as polyoxyethylated lauric acid (U.S. Pat. Nos. 3,853,465 and 4,184,848). Since only surfactants were used, a rather high concentration of surfactant was needed for an effective clearing. High concentration of surfactants are often interacted with other chemical or enzyme reactions and causes complication of analysis.

In the present invention, a relative low concentration of surfactant is used. This is accomplished by the action of enzyme (cholesterol esterase or lipase) added to the clearing reagent.

The exact mechanism of clearing by this invention is not yet known. It is possible to speculate however that, in cases where patients have hyperlipemia, the turbidity found in serum samples is due primarily to an elevated triglyceride content.

Triglycerides are water-insoluble, and usually buried inside the fat core with cholesterol esters in lipoprotein complex. The clearing of a lipemic sample must be brought about by the disrupture of lipoprotein by a surfactant such as lauric acid diethanolamide (DEA), followed by the hydrolysis of triglycerides by the enzyme base. The surfactant also aids the dissolution of fatty acids released therein. Without enzyme, there is no clearing.

It is the object of this invention to provide a reagent which is effective in clearing turbidity in biological samples and to a method of effecting same, particularly in cases where the sample is to be photometrically assayed or analyzed for a particular component such as cholesterol.

SUMMARY OF THE INVENTION

In accordance with this invention, there is claimed a reagent effective in clearing turbidity of a biological sample comprising a surfactant of the formula:

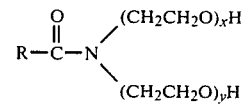

wherein R is alkyl or alkenyl containing from 5 to 17 carbon atoms, x and y are each 1; and an enzyme selected from cholesterol esterase or lipase or mixtures thereof.

Preferably, the above reagent in aqueous buffered form will comprise from about 0.05 g/dl to about 2.5 g/dl of surfactant, and preferably from 0.1 g/dl to about 0.5 g/dl, and at least about 0.025 U/ml of enzyme (cholesterol esterase based on the total formulation. The resulting formulation will have a pH in the range from about 5.5 to about 7.0.

When the formulation contains a lipase enzyme, the surfactant comprises from about 0.05 g/dl to about 2.5 g/dl, and preferably from 0.1 g/dl to about 0.5 g/dl, and said enzyme comprises at least about 1.0 U/ml of the resulting formulation, said formulation having a pH in the range from about 5.5 to about 8.0.

In both enzyme formulations, the buffer employed can be a maleate, in the form of the sodium or potassium salt; a phosphate; a borate; a citrate; a succinate; an imidazoleacetate buffer; Tris; etc. Any suitable buffer can be used however. Such buffer is any one which will maintain a constant pH in the desired range without interfering with any of the components.

When a maleate buffer is used, e.g. the potassium or sodium salt, it is added in amounts to provide from about 0.05M to about 0.5M and the pH of the resulting formulation is from about 5.0 to about 7.0.

Similar concentrations are used for the other buffers.

In addition to the above components, a solubility enhancer can be included in the above enzyme formulations. Such enhancer comprises any material which aids the surfactant in solubilization. For example, bile salts are particularly effective such as sodium cholate, sodium deoxycholate, etc.

In another preferred embodiment the surfactant is of the above formula in which R is alkyl such as lauric acid diethanolamide or oleic acid diethanolamide.

The enzyme is derived from animal, e.g. animal pancreatic tissue or microbial source.

Biological samples suitably treated include human serum and plasma.

The reagent described above when combined with a biological sample results in an effective turbidity-clearing effect. The reagent is commonly provided in aqueous buffered form.

Also within the purview of this invention is a reagent, effective in clearing turbidity of a biological sample to be photometrically assayed or analyzed which comprises at least one surfactant of the formula:

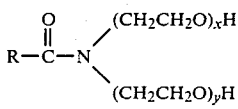

wherein R is alkyl or alkenyl containing from 5 to 17 carbon atoms, x and y are whole number integers whose sum is no greater than 11; and an enzyme selected from cholesterol esterase or lipase or mixtures thereof.

A preferred reagent is one having a surfactant of the above formula in which R is alkyl, preferably lauryl, and the sum of x and y is 5 and the enzyme is a lipase. Formulations with this reagent desirably include polyethylene glycol p-isooctyl phenyl ether or other suitable surfactants.

Another preferred reagent which will produce effective clearing of turbid samples in the pH range of 2 to 10 is a mixture of two surfactants, namely, lauric acid diethanolamide ($x=y=1$) and epoxylated lauric acid ($x+y=5$).

Enzyme formulations as previously described are prepared using the surfactant shown above.

Suitable surfactants embraced by the above formula include lauric acid diethanolamide, myristic acid diethanolamide, capric acid diethanolamide, oleic acid diethanolamide and coco acid diethanolamide.

This reagent when combined with a biological sample effectively clears turbidity in the sample and allows it to be accurately photometrically assayed or analyzed. In this manner, a sample to be photometrically analyzed for cholesterol is beneficially treated.

DETAILED DESCRIPTION OF THE INVENTION

The present invention, in one aspect, involves a reagent and method which effectively clear turbidity of a biological sample by the employment of a particular surfactant and enzyme. In this aspect, the surfactant has the formula:

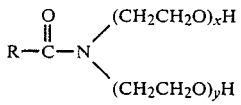

wherein R is alkyl or alkenyl of from 5 to 17 carbon atoms, x and y are each 1. Preferably, R is alkyl exemplified by lauric acid diethanolamide.

The enzyme component is cholesterol esterase or lipase or mixtures of the two.

The resulting formulation has been found, quite surprisingly, to be highly effective in clearing turbidity in a biological sample. It is therefore enormously useful in converting a biological specimen which is turbid to one which is clear.

The sample so treated can be colorimetrically assayed or analyzed for any particular component so long as the reagents employed in the assay do not inhibit or interfere with the interaction between surfactant and enzyme and vice-versa.

Typical assays that can be carried out utilizing the above reagent include cholesterol, triglycerides and creatine phosphate kinase determinations.

The enzyme component can be derived from an animal source such as pancreatic tissue or microbial source.

In a second aspect of this invention, a reagent and method are taught which effectively clear a turbid biological sample which is to be photometrically assayed. The reagent includes at least one surfactant, more broadly defined than above, having the formula:

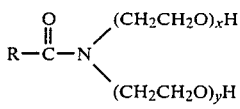

wherein R is alkyl or alkenyl containing from 5 to 17 carbon atoms, x and y are whole number integers whose sum is no greater than 11; and an enzyme selected from cholesterol esterase or lipase or mixtures thereof.

In a preferred embodiment, the surfactant is as above in which R is alkyl and x and y are each 1. Examples of the latter include lauric acid diethanolamide, myristic acid diethanolamide and capric acid diethanolamide. Also preferred are surfactants in which R is alkenyl and x and y are 1 such as oleic acid diethanolamide and coco acid diethanolamide. In another preferred embodiment, the surfactant is as above in which R is alkyl and the sum of x and y is 5.

The enzyme component can be derived from an animal source such as pancreatic tissue or from a microbial source.

When the above reagent is employed for assaying purposes, it is combined in aqueous buffered form with a biological sample. The turbid sample is cleared and is ready for the assay.

Samples which are efficiently cleared and prepared for assay include human serum and plasma.

The method and reagent of this invention are unique in at least two respects. They permit the determination of components in biological samples in a clear free state without turbidity interferences and, in addition, because of the interaction between the particular surfactant and enzyme employed, permit one to use lesser amounts of enzyme than are normally used in the case of cholesterol determination. In this latter regard, the employment of smaller amounts without lessening in rates of reaction can be viewed as an improvement in the rate of enzymatic reaction.

The most common clinical determination of cholesterol in a biological fluid is the total cholesterol which includes both free cholesterol and cholesterol esters. Both cholesterol and its esters are present in serum with other lipids and various proteins in micromolecular complexes called lipoproteins and cholesterol esters normally exist as a major component (60-80%) of the total cholesterol. They are generally water insoluble and are normally buried inside the complex and inaccessible to enzymes. In the determination of total cholesterol by a wholly enzymic method, whether automated or manual, both cholesterol and cholesterol esters must first be liberated by a suitable surfactant. Cholesterol esters are then hydrolyzed by cholesterol esterase to yield free cholesterol which is, in turn, oxidized by cholesterol oxidase to form cholestenone and hydrogen peroxide.

The herein disclosed method can be applied in automated fashion as by the employment of an automatic analyzer or it can be done manually.

In preparing the formulations for use in assaying by the method of this invention, an aqueous solution is formulated which contains, in addition to the surfactant and enzyme, other reference materials which are known in the art and are utilized for such purpose.

For example, in cholesterol assaying, the following components are employed in the ranges shown hereinbelow:

| Component | Cholesterol Assay |
| --- | --- |
| Peroxidase | 0.8–2.0 U/l |
| Cholesterol oxidase | 0.025–0.3 U/ml |
| Cholesterol esterase | .025–.3 U/ml |
| Surfactant | .05–.5 g/dl |
| Sodium cholate | 0.05–0.5 g/dl |
| Sodium p-Hydroxybenzoate | 2.5–6 g/dl |
| 4-Aminoantipyrine | 0.5–2.0 mM |
| Maleic acid | 0.1–0.5 M |
| pH | 5.5–7.0 |
| Sample/Reagent ratio | 100–400 |

In the above formulation, it is preferred to use cholesterol esterase from an animal source, e.g. pancreas; however, equivalent results are obtained with cholesterol esterase from a microbial source.

EXAMPLE I

Clearing as a function of cholesterol esterase

Three ml of clearing reagent which contains potassium-maleate (0.1M), sodium cholate (0.25 g/dl), lauric acid diethanolamide (0.2 g/dl), cholesterol esterase (0.08 U/ml to 0.8 U/ml) final pH 6.0 is mixed with 0.025 ml of lipemic serum (triglycerides or about 1400 mg/dl). The reaction mixture turns clear, within 10 minutes at 45° C. The cholesterol esterase for clearing can be from pancreas or microorganisms.

EXAMPLE II

Use for cholesterol determination

For end point chemistry as illustrated in this example the ingredients for cholesterol assay are thus included into the clearing reagent.

Three ml of a formulation which contains cholesterol esterase (0.125 U/ml), cholesterol oxidase (0.125 U/ml), peroxidase (1.6 U/ml), 4-aminoantipyrine (0.6 mM), sodium hydroxybenzoate (25 mM), sodium cholate (0.25 g/dl), lauric acid diethanolamide (0.2 g/dl) and potassium maleate (0.1M), pH 6.0. This whole reagent is mixed with 0.025 ml of lipemic serum sample. The mixture is then incubated at 45° C. for 4–5 minutes. The total cholesterol is then determined by measuring the color intensity at 520 nm. Without the clearing effect of lauric acid diethanolamide and cholesterol esterase, the determination of cholesterol in turbid samples always gives erroneous results.

EXAMPLE III

Clearing by candida lipase (candida cylindracea)

Three ml of a clearing reagent containing lauric acid diethanolamide (0.2 g/dl), Na cholate (0.25 g/dl) and lipase (25 U/ml) and maleate buffer (0.1M), pH 6.0, are mixed with 0.025 ml lipemic serum. The turbid sample will turn clear after 5 minutes incubation at 45° C.

When an equivalent amount of clearing agent comprising a mixture of lauric acid diethanolamide and epoxylated lauric acid (x+y=5) is used, comparable clearing results.

EXAMPLE IV

Three ml of a clearing reagent containing a surfactant of the formula:

$$C_{11}H_{25}-\overset{O}{\overset{\|}{C}}-N\diagup^{(CH_2CH_2O)_xH}_{(CH_2CH_2O)_yH}$$

in which x+y=5 (0.2 g/dl), Triton X-100 (0.4 g/dl), potassium maleate (0.2M) and lipase (25 U/ml), pH 6.0, is mixed with 0.05 ml lipemic sample and incubated at 45° C. The turbid sample turns clear after 3 minutes.

The rate of clearing is enhanced by increasing the buffer concentration.

Similar results are obtained by using higher concentrations of epoxylated lauric acid (x+y=5) without the assistance of Triton X-100.

EXAMPLE V

A. Formulation

A diagnostic reagent formulation is prepared as a one liter aqueous solution using the following ingredients.

| Ingredient | Concentration |
| --- | --- |
| Malic Acid | 11.6 g |
| KOH | 10.0 g |
| EDTA (K$_2$) | 2.7 mM |
| Na Cholate | 5.8 mM |
| Na p-Hydroxybenzoate | 25.0 mM |
| 4-Aminoantipyrine | 0.6 mM |
| Lauric Acid Diethanolamide | 2.0 g |
| Cholesterol Esterase | 125 Units |
| Cholesterol Oxidase | 125 Units |
| Horseradish Peroxidase | 800 Units |

The pH is adjusted to a pH of 6.

The reagent system may be stored and used in the form of an aqueous solution or the solution may be freezedried by conventional means and reconstituted with water when ready for use.

B. Assay-Total Cholesterol Determination

Three ml of the above reagent is mixed with 0.025 ml of serum or reconstituted serum standard which contains up to 500 mg/dl cholesterol. The reaction is carried out at 45° C. for 4 to 5 minutes. The absorbance of samples at 525 nm is measured against the reagent blank.

EXAMPLE VI

Clearing in determination of creatine phosphate kinase (CPK) activity of lipemic serum Two ml of imidazole-acetate buffer, 0.1M, pH 6.7 containing lauric acid diethanolamide (0.4%), pancreatic cholesterol esterase (25 U/dl), Na Cholate (0.25 g%) and thiolglycerol (20 mM), is mixed with 0.05 ml of lipemic serum. After 15 minutes incubation at 37° C., the turbidity at 340 nm drops from 2.3 O.D. to 0.02 O.D. The clear sample is then mixed with 1 ml of CPK reagent which contains Creatine Phosphate (116.7 mM), ADP (6.7 mM), AMP (16.7 mM), EDTA (6.7 mM), NADP (6.7 mM), Hexokinase (125 U/dl), glucose 6-phosphate dehydrogenase, G6PDH (100 U/dl) prepared in 0.1M imidazole-acetate buffer, pH 6.7. The activity of CPK is monitored at 340 nm and 37° C. as the conventional method.

It should be understood by those skilled in the art that various modifications may be made in the present inven-

What is claimed is:

1. In an assay for a component in serum or plasma samples comprising mixing sample with reagent and determining the amount of component therein, the improvement comprising a separate pretreatment step which includes adding the enzymes cholesterol esterase, lipase or mixtures thereof and at least one surfactant of the formula:

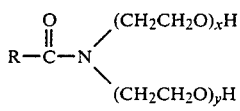

wherein R is alkyl or alkenyl containing from 5 to 17 carbon atoms; and x and y are whole number integers whose sum is no greater than 11 under conditions which permit sample clarification and wherein the amount of said enzyme and said surfactant when combined are sufficient to effectively clear turbidity from the untreated serum or plasma sample.

2. The assay of claim 1 wherein said sample is a human serum sample.

3. The assay of claim 1 wherein said conditions comprise incubation at a temperature between room temperature and 45° C.

4. The assay of claim 1 wherein said surfactant is of the formula wherein x and y are each 1, the enzyme is cholesterol esterase, and the resulting formulation in aqueous buffered form, comprises from about 0.05 g/dl to about 2.5 g/dl of surfactant and at least about 0.025 U/ml of enzyme, said formulation having a pH in the range from about 5.5 to about 7.0.

5. The assay of claim 4 wherein said surfactant comprises from about 0.1 g/dl to about 0.5 g/dl of the resulting formulation.

6. The assay of claim 4 wherein the buffer is a maleate used in a concentration of from about 0.05M to about 0.5M and the pH of the resulting formulation is from about 5.0 to about 7.0.

7. The assay of claim 4 wherein said formulation includes a solubility enhancer.

8. The assay of claim 7 in which said solubility enhancer is sodium cholate or sodium deoxycholate in an amount to provide about 0.25 g/dl of the total formulation.

9. The assay of claim 1 wherein said surfactant is of the formula wherein x and y are each 1, the enzyme is a lipase, and the resulting formulation, in aqueous buffered form, comprises from about 0.05 g/dl to about 2.5 g/dl of surfactant and at least about 1.0 U/ml of enzyme, said formulation having a pH in the range from about 5.5 to about 8.0.

10. The assay of claim 9 wherein said surfactant comprises from about 0.1 g/dl to about 0.5 g/dl of the resulting formulation.

11. The assay of claim 9 wherein the buffer is a maleate used in a concentration of from about 0.05M to about 0.5M and the pH of the resulting formulation is from about 5.0 to about 7.0.

12. The assay of claim 9 wherein said formulation includes a solubility enhancer.

13. The assay of claim 12 in which said solubility enhancer is sodium cholate or sodium deoxycholate in an amount to provide about 0.25 g/dl of the total formulation.

14. The assay of claim 1 wherein said surfactant is of the formula in which R is alkyl and x and y are each 1.

15. The assay of claim 14 wherein said surfactant is lauric acid diethanolamide.

16. The assay of claim 14 wherein said surfactant is myristic acid diethanolamide.

17. The assay of claim 14 wherein said surfactant is capric acid diethanolamide.

18. The assay of claim 1 wherein said surfactant is of the formula in which R is alkenyl and x and y are each 1.

19. The assay of claim 18 wherein said surfactant is oleic acid diethanolamide.

20. The assay of claim 18 wherein said surfactant is coco acid diethanolamide.

21. The assay of claim 1 in which said enzyme is derived from animal or microbial source.

22. The assay of claim 21 in which said enzyme is cholesterol esterase derived from animal pancreatic tissue.

23. The assay of claim 1 wherein the surfactant is of the formula wherein x+y is no greater than 5, the enzyme is cholesterol esterase, and the resulting formulation, in aqueous buffered form, comprises from about 0.05 g/dl to about 2.5 g/dl of surfactant and at least about 0.025 U/ml of enzyme, said formulation having a pH in the range from about 5.5 to about 8.0.

24. The assay of claim 23 wherein the buffer is a maleate used in a concentration of from about 0.05M to about 0.5M and the pH of the resulting formulation is from about 5.0 to about 7.0.

25. The assay of claim 1 wherein the surfactant is of the formula wherein x+y is no greater than 5, the enzyme is a lipase, and the resulting formulation, in aqueous buffered form, comprises from about 0.05 g/dl to about 0.5 g/dl of surfactant and at least about 1.0 U/ml of enzyme, said formulation having a pH in the range from about 2.0 to about 10.0.

26. The assay of claim 25 wherein the buffer is selected from maleate, citrate, succinate, Tris or borate used in a concentration of from about 0.05M to about 0.5M and the pH of the resulting formulation is from about 2.0 to about 10.0.

27. The assay of claim 1 in which said enzyme is derived from animal or microbial source.

28. The assay of claim 27 in which said enzyme is cholesterol esterase derived from animal pancreatic tissue.

29. The assay of claim 1 wherein the surfactant is of the formula in which R is alkyl, the sum of x and y is 5, and said enzyme is a lipase.

30. The assay of claim 29 which includes polyethylene glycol p-isooctyl phenyl ether (Triton X-100).

31. The assay of claim 1 wherein the surfactant comprises a mixture of lauric acid diethanolamide and epoxylated lauric acid (x+y=5) and the resulting formulation, in aqueous buffered form, comprises from about 0.05 g/dl to about 2.0 g/dl of surfactant, said formulation having a pH in the range from about 2.0 to about 10.0.

* * * * *